United States Patent
Buan et al.

(10) Patent No.: US 10,881,553 B1
(45) Date of Patent: Jan. 5, 2021

(54) REDUCED PRESSURE DEVICE HAVING SELECTIVELY DELIVERABLE ELECTROLYTE

(71) Applicant: Advanced Dressing, LLC, Cleveland, OH (US)

(72) Inventors: John Buan, Maple Grove, MN (US); Richard L. Middaugh, Rocky River, OH (US); Timothy Wojciechowski, Westlake, OH (US); Thomas E. Lash, Chardon, OH (US)

(73) Assignee: Advanced Dressing, LLC, Cleveland, OH (US)

( * ) Notice: Subject to any disclaimer, the term of this patent is extended or adjusted under 35 U.S.C. 154(b) by 0 days.

(21) Appl. No.: 16/592,142

(22) Filed: Oct. 3, 2019

(51) Int. Cl.
*A61F 13/00* (2006.01)
*A61M 1/00* (2006.01)

(52) U.S. Cl.
CPC ....... *A61F 13/00068* (2013.01); *A61M 1/009* (2014.02); *A61M 1/0025* (2014.02); *A61F 2013/00119* (2013.01); *A61M 2205/3331* (2013.01)

(58) Field of Classification Search
CPC ...... A61F 13/00068; A61F 2013/00119; A61F 7/034; A61F 2007/036; A61F 2007/038; A61M 1/009; A61M 1/0025; A61M 2205/3331; A61M 2205/0277; A61M 2205/364; A61M 2202/0208; A61H 2201/0278
See application file for complete search history.

(56) References Cited

U.S. PATENT DOCUMENTS

| | | | | |
|---|---|---|---|---|
| 2,157,169 A | * | 5/1939 | Foster | A47J 36/30 126/263.01 |
| 3,635,567 A | * | 1/1972 | Richardson, Jr. | A47K 7/03 401/132 |
| 4,559,921 A | * | 12/1985 | Benmussa | A45C 11/20 126/263.09 |
| 4,771,761 A | * | 9/1988 | Doukhan | A47J 36/28 126/246 |
| 6,000,403 A | * | 12/1999 | Cantwell | A61M 35/006 128/888 |
| 6,341,602 B1 | * | 1/2002 | Fulcher | A47J 36/28 126/263.07 |
| 6,890,553 B1 | | 5/2005 | Sun et al. | |
| 9,447,987 B1 | * | 9/2016 | Arvey | F23L 13/00 |
| 10,046,095 B1 | * | 8/2018 | Middaugh | C25B 1/00 |

(Continued)

FOREIGN PATENT DOCUMENTS

WO    WO-2017075381 A1 *  5/2017  ....... A61F 13/00068

*Primary Examiner* — Adam Marcetich
(74) *Attorney, Agent, or Firm* — Rankin, Hill & Clark LLP

(57) ABSTRACT

A reduced pressure device includes a dressing and a reactor. The dressing covers a dressing site and defines an enclosed volume beneath the dressing and around the dressing site. The reactor is disposed with respect to the dressing so as to produce a reduced pressure beneath the dressing when activated. The reactor includes a reducing agent and an electrolyte solution. The electrolyte solution is configured to be selectively delivered to the reducing agent, and the reactor begins to react with at least one selected gas in the enclosed volume after the electrolyte solution is delivered to the reducing agent to consume the at least one selected gas within the enclosed volume.

5 Claims, 10 Drawing Sheets

(56) References Cited

U.S. PATENT DOCUMENTS

| | | | | |
|---|---|---|---|---|
| 2002/0197094 A1* | 12/2002 | Gruenbacher | ........... | A47K 7/03 |
| | | | | 401/133 |
| 2005/0070835 A1* | 3/2005 | Joshi | ................. | A61M 1/0066 |
| | | | | 602/41 |
| 2006/0005827 A1* | 1/2006 | Consoli | .................... | C09K 5/18 |
| | | | | 126/263.06 |
| 2006/0155251 A1* | 7/2006 | Assie | ................... | A61F 13/0203 |
| | | | | 604/306 |
| 2006/0258962 A1* | 11/2006 | Kopanic | ............ | A61H 23/0263 |
| | | | | 601/15 |
| 2007/0265586 A1* | 11/2007 | Joshi | ................... | A61M 1/0035 |
| | | | | 604/313 |
| 2009/0326622 A1* | 12/2009 | Johnson | .................. | A61F 7/032 |
| | | | | 607/111 |
| 2011/0257572 A1* | 10/2011 | Locke | ................ | A61M 1/0052 |
| | | | | 602/46 |
| 2012/0180777 A1* | 7/2012 | Young | ................ | B65D 81/3272 |
| | | | | 126/263.01 |
| 2014/0018753 A1* | 1/2014 | Joshi | ....................... | A61L 15/60 |
| | | | | 604/319 |
| 2015/0232254 A1* | 8/2015 | Huffer | ..................... | A61F 7/034 |
| | | | | 206/484.2 |
| 2018/0318137 A1* | 11/2018 | Donda | ................ | A61M 1/0088 |
| 2018/0318165 A1* | 11/2018 | Donda | ................ | A61M 1/0088 |

* cited by examiner

REDUCED PRESSURE DEVICE HAVING SELECTIVELY DELIVERABLE ELECTROLYTE

BACKGROUND

Negative pressure and reduced pressure are terms used to describe a pressure that is below normal atmospheric pressure. Negative pressure wound therapy ("NPWT") is utilized for several sites on the skin, such as a wound or an incision. Furthermore, NPWT is useful to manage wounds with complex healing concerns.

Negative or reduced pressure therapy may also be used for a therapeutic treatment that utilizes negative pressure for skin treatments and restorative purposes. In these instances the pressure used for skin treatments and restorative purposes may not need to be as low (offset from normal atmospheric pressure) as that used in NPWT. For example, where −80 mmHg to −125 or even −150 mmHg may be desired for NPWT, for skin treatments and restorative purposes the pressure may need to be reduced to only −20 mmHg or −40 mmHg. As such, simply a reduced pressure may be desired in some instances, even including instances where a wound may be treated.

It is known to use a vacuum generation source, such as an electromechanical pump, to apply reduced pressure to the inside of a dressing on a dressing site. However, when a vacuum source operates using a chemical reaction in which a gas found in air is consumed to as to reduce the pressure at the dressing site, it is known to isolate a substrate impregnated with a reducing agent and an electrolyte solution from air using an air-tight foil packet. When it is desired to begin the chemical reaction, the substrate is exposed to air by tearing or removing a section of the air-tight foil packet. However, other manners to activate the chemical reaction may be desirable.

SUMMARY

In view of the foregoing, a reduced pressure device includes a dressing and a reactor. The dressing covers a dressing site and defines an enclosed volume beneath the dressing and around the dressing site. The reactor is disposed with respect to the dressing so as to produce a reduced pressure beneath the dressing when activated. The reactor includes a reducing agent and an electrolyte solution. The electrolyte solution is configured to be selectively delivered to the reducing agent, and the reactor begins to react with at least one selected gas in the enclosed volume after the electrolyte solution is delivered to the reducing agent to consume the at least one selected gas within the enclosed volume.

DETAILED DESCRIPTION

Figure 1:
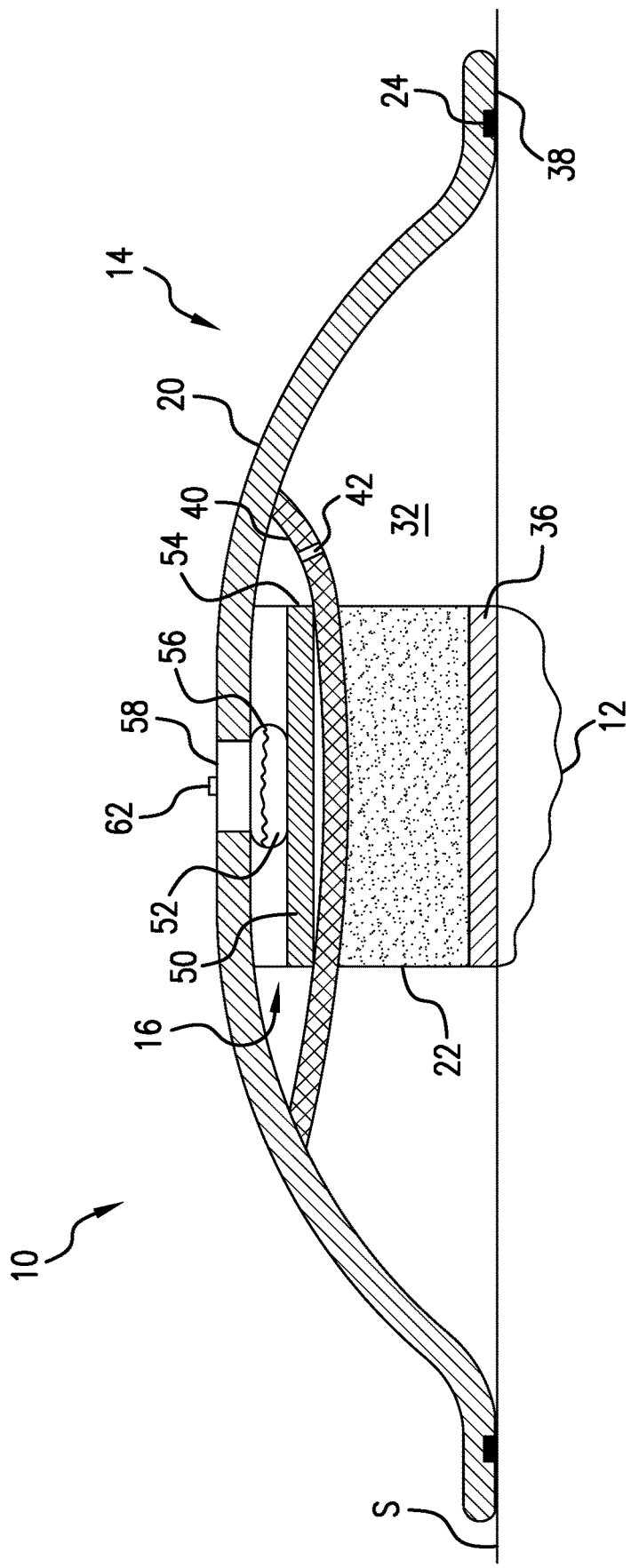
FIG. 1 is a schematic cross-sectional view of a reduced pressure device.

FIG. 1 depicts a reduced pressure device 10 useful for administering negative and/or reduced pressure therapy to a dressing site 12. Reduced pressure described herein is pressure below atmospheric pressure. The reduced pressure device 10 includes a dressing 14 and a reactor 16, which operates as a vacuum source. The dressing 14 is placed over the dressing site 12 on a patient's skin S. The dressing site 12 can be, but is not limited to, a wound, an incision, or skin where there is no wound or incision, for example in a cosmetic application. The reduced pressure device 10, which can be used for NPWT or for instances where the pressure need not be reduced to what is typically achieved in NPWT, generally includes the dressing 14, the reactor 16, a drape 20, an absorbent element 22, and a sealing element 24. The dressing 14 may further include valves, pressure indicators and the like.

The drape 20 can be made from a flexible material and can be a thin film capable of maintaining a reduced pressure underneath the drape 20 upon application of a vacuum. The thin film from which the drape 20 is made can be substantially impermeable to liquids but somewhat permeable to water vapor, while still being capable of maintaining reduced pressure underneath the drape 20. For example, the thin film material from which the drape 20 is made may be constructed of polyurethane or other semi-permeable material such as that sold under the Tegaderm® brand or 9834 TPU tape available from 3M. Similar films are also available from other manufacturers. The drape 20 can be made in a variety of shapes and sizes to cover a variety of dressing sites 12.

The absorbent element 22 is made from an absorbent material that is capable of absorbing exudate from the dressing site 12. The absorbent element 22 can be made from super absorbent acrylate, absorbent beads, foams, or natural absorbents. The absorbent element 22 can also be a hydroactive wound pad available under the trademark Vilmed®, which chemically absorbs exudate and precludes the exudate from passing through the absorbent element 22 toward the reactor 16 unlike a sponge.

The sealing element 24 cooperates with the drape 20 and skin S to create an enclosed volume 32 defined between the drape 20 and the dressing site 12 and surrounded by the sealing element 24. The reactor 16, which when activated operates as a vacuum source in fluid communication with the enclosed volume 32, administers reduced pressure to the enclosed volume 32 so as to control the atmosphere within the enclosed volume 32. The sealing element 24 can be separate from the dressing 14 or can instead be a component of the dressing 14. The sealing element 24 functions like a gasket, as the sealing element 24 prevents fluid (including air) from escaping between the drape 20 and the skin S. The sealing element 24 can be made from a material such as silicone or a hydrogel material, for example.

The dressing 14 may further include a wound contact layer 36. The wound contact layer 36 can be made of an elastomeric material, such as a polymeric material that has rubber-like properties. Furthermore, the wound contact layer 36 can be an elastomeric material that is a thin, flexible elastomeric film. Some examples of such materials include a silver coated nylon, a perforated silicone mesh, or other material that will not stick to the patient's tissue. The wound contact layer 36 can also be a polyurethane film layer in which holes can be provided. A silicone coating can also be provided on a skin-contacting side of the absorbent element 22 instead of the wound contact layer 36.

A drape release liner (not shown in FIG. 1) is disposed on a bottom surface of the drape 20. The drape release liner is removed before the dressing 14 is applied to the dressing site 12. When the drape release liner is removed, an adhesive 38 on the bottom surface of the drape 20 is exposed. As the dressing 14 is placed on the patient, the adhesive 38, which can be an acrylic-based adhesive that is distinct from the sealing element 24, secures the drape 30 to the patient's skin S around the dressing site 12. Thus, contact is maintained between the drape 20 and the skin S.

Figure 2:
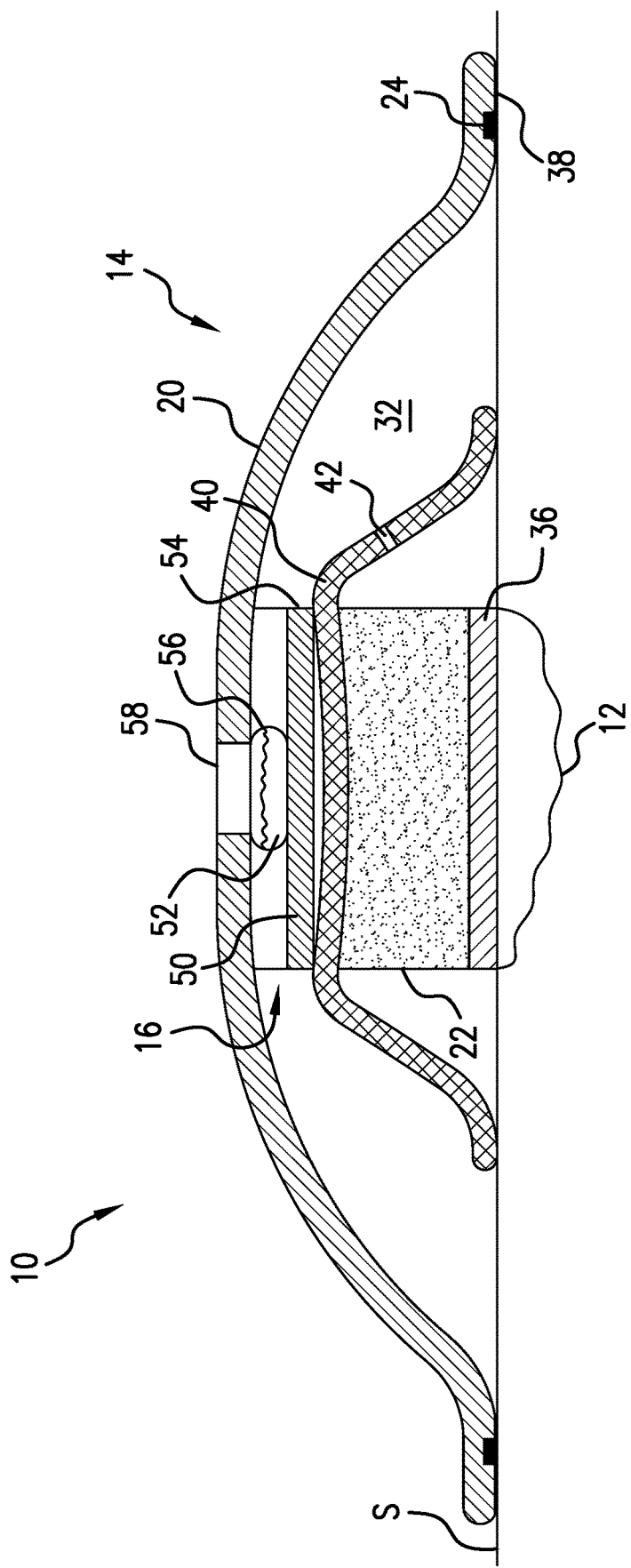
FIG. 2 is a schematic cross-sectional view of the reduced pressure device according to an alternative arrangement.

The dressing 14 may also include a membrane 40 between the reactor 16 and the absorbent element 22. In the embodiment shown in FIG. 1, the membrane 40, which can be a thin film similar to the drape 20, is fixed to the bottom surface of the drape 20. The membrane 40 includes at least one opening 42 or is pervious to air so that air is allowed to travel through the membrane 40. Therefore, the reactor 16 is in fluid communication with the enclosed volume 32. In an alternative embodiment shown in FIG. 2, the membrane 40 can disposed over the dressing site 12 with the absorbent element 22 affixed to it. In this alternative embodiment, the dressing 14 can be what may be referred to as a two-piece dressing in which the membrane 40 and the absorbent element 22 are placed on the patient's skin S over the dressing site 12, and then the drape 20 and the components affixed thereto are placed over the membrane 40 and the dressing site 12. In the embodiment depicted in FIG. 2, the membrane 40 would include an adhesive on a lower surface to allow the membrane to adhere to the skin S. The membrane 40 may also include a sealing element (similar to the sealing element 24) which would allow the drape 20 to be adhered and sealed to the membrane 40 instead of the skin S.

The reactor 16 is configured to react with at least one selected gas found in air to remove the selected gas from air. The reactor 16 is located with respect to the drape 20 and the sealing element 24 so that the reactor 16 can be in fluid communication with the enclosed volume 32. The reactor 16 consumes the selected gas from the enclosed volume 32 thereby removing the selected gas and reducing the gas pressure. For example, the reactor 16 can be an oxygen scavenger which removes oxygen from the air within the enclosed volume 32 so as to reduce gas pressure within the enclosed volume 32 by approximately 20%. Since the vacuum source in this embodiment is the reactor 16 that consumes a gas found in air (as opposed to a mechanical pump), any leakage around the enclosed volume 32 is important to prevent. Uncontrolled ingress of outside oxygen, which could prematurely use up the reactor 16, should be prevented or limited from penetrating either through the drape 20 or the sealing element 24 or between the sealing element 24 and the skin S.

The reactor 16 includes a reducing agent 50, such as aluminum, zinc or iron, and an electrolyte solution 52. An example of a substrate impregnated with a reducing agent and an electrolyte solution is found in U.S. Publication No. 2014/0109890A1. Unlike the heater described in U.S. Publication No. 2014/0109890A1 in which a substrate having the reducing agent and a pad impregnated with the electrolyte solution are packaged in a hermetically sealed foil package, the electrolyte solution 52 is shielded from the reducing agent 50 until reduced pressure beneath the dressing 14 is ready to be administered obviating the need for the hermetically sealed foil package. When reduced pressure therapy is ready to be administered to the dressing 14, the electrolyte solution 52 is introduced to the reducing agent 50. The reactor 16 then begins to react with the at least one selected gas, e.g., oxygen, in the enclosed volume 32 to create reduced pressure at the dressing site 12. As illustrated in FIG. 1, the dressing 14 may further include a substrate 54 that includes the reducing agent 50 and a binding agent, such as polytetrafluoroethylene or a polyolefin. The term "substrate" means that the substrate 54 is a solid object, and not merely a mass of powdered chemicals; however, the reducing agent 50 could be provided in the dressing 14 as a mass of powdered chemicals, if desired.

Figure 3:
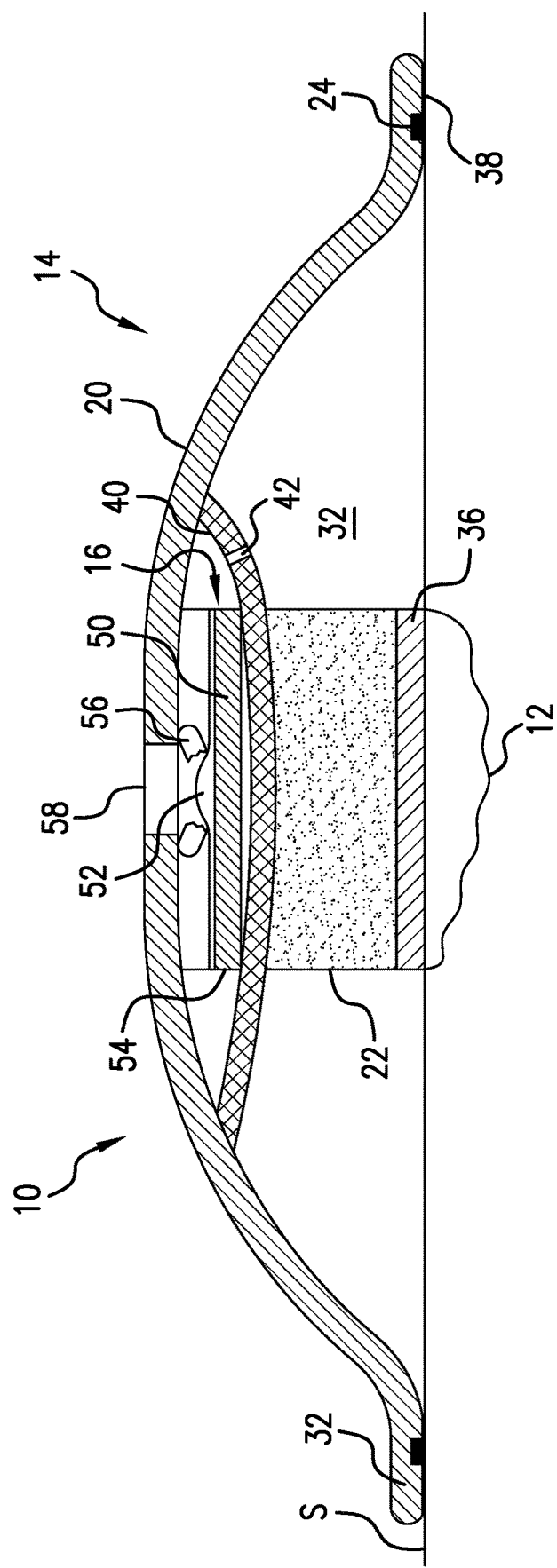
FIG. 3 is schematic cross-sectional view of a reduced pressure device after rupturing a capsule.

In FIG. 1, the electrolyte solution 52 is stored in a rupturable capsule 56 disposed adjacent to the reducing agent 50. The capsule 56 can be any package that can be selectively ruptured to allow liquid contents disposed therein to leak from the package after it is ruptured. The user presses onto a pressing location 58 on the drape 20 over the capsule 56 to break the capsule 56. Once the capsule 56 is broken, which is shown in FIG. 3, the electrolyte solution 52 is delivered to the reducing agent 50, and the reducing agent 50 begins to react with the at least one selected gas in the enclosed volume 32 so as to consume the selected gas from the enclosed volume 32. The drape 20 may include a marking 62 disposed on a top surface of the drape 20 above the capsule 56 to indicate where the pressing location 58 is located to provide an indication to a user of the pressing location 58. The marking 62 may be a circle disposed around a periphery of the pressing location 58; however, the marking 62 can be any marking that indicates to a user where the pressing location 58 is located. A button may also be provided at the pressing location 58.

Figure 4:
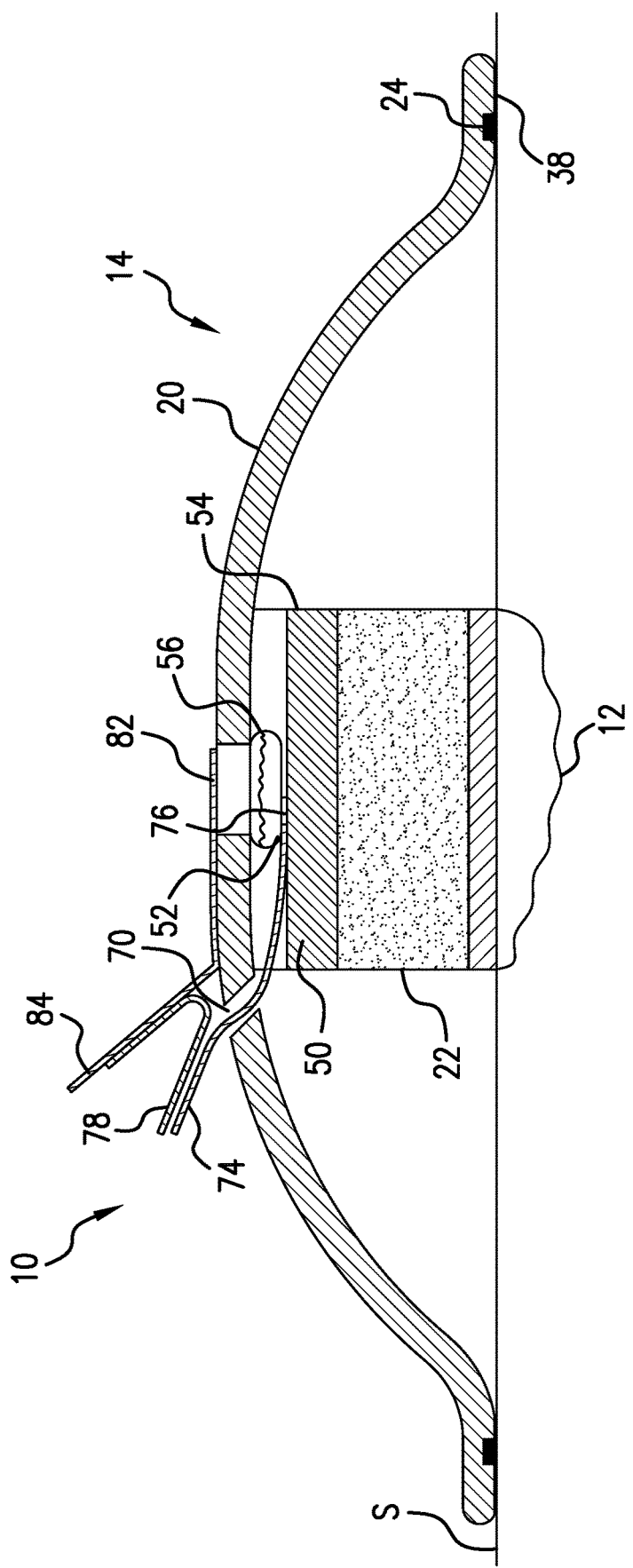
FIG. 4 is a schematic cross-sectional view of another reduced pressure device.

With reference to FIG. 4, in another embodiment, an opening, which is in the form of a slit 70 in the illustrated embodiment, is disposed on the drape 20. A first pull tab 74 extends from beneath the drape 20 to ambient through the slit 70 and is connected to a separable layer 76 of the capsule 56. The separable layer 76 isolates the electrolyte solution 52 within the capsule 56 and from the reducing agent 50. The first pull tab 74, which could also be in the form of a string, can be pulled to remove the first pull tab 74 and the separable layer 76 from the slit 70. When the first pull tab 74 is pulled, the separable layer 76 is removed from the capsule 56 and, if desired, from the enclosed volume 32 through the slit 70, exposing the reducing agent 50 to the electrolyte solution 52. After the removal of the separable layer 76, the electrolyte solution 52 is delivered to the reducing agent 50, which begins to react with a selected gas, e.g., oxygen, in the enclosed volume 32.

A second pull tab 78 is connected to a cover layer, which can be a thin film 82 placed over and adhered to a portion of the top surface of the drape 20. The thin film 82 could be made integral with the drape 20. The thin film 82 can include a flap 84 and, as depicted in FIG. 4, the slit 70 is disposed underneath the flap 84. The second pull tab 78 can be connected to or provided as a release layer provided on a bottom surface of the thin film 82 in the region of the flap 84. The release layer covers an adhesive (not visible in FIG. 4) on a bottom surface of the thin film 82. When the second pull tab 78 is pulled, which occurs after the first pull tab 74 has been removed from the slit 70, the second pull tab 78 disconnects the release layer from the flap 84 and the adhesive disposed on the bottom surface of the flap 84 is exposed. The flap 84 is then moved towards the drape 20 to cover the slit 70. When the thin film 82 covers the slit 70, the reactor 16 is closed off from ambient and reacts with the selected gas found in the enclosed volume 32 under the dressing 14. Reduced pressure is therefore developed in the enclosed volume 32.

Figure 5:
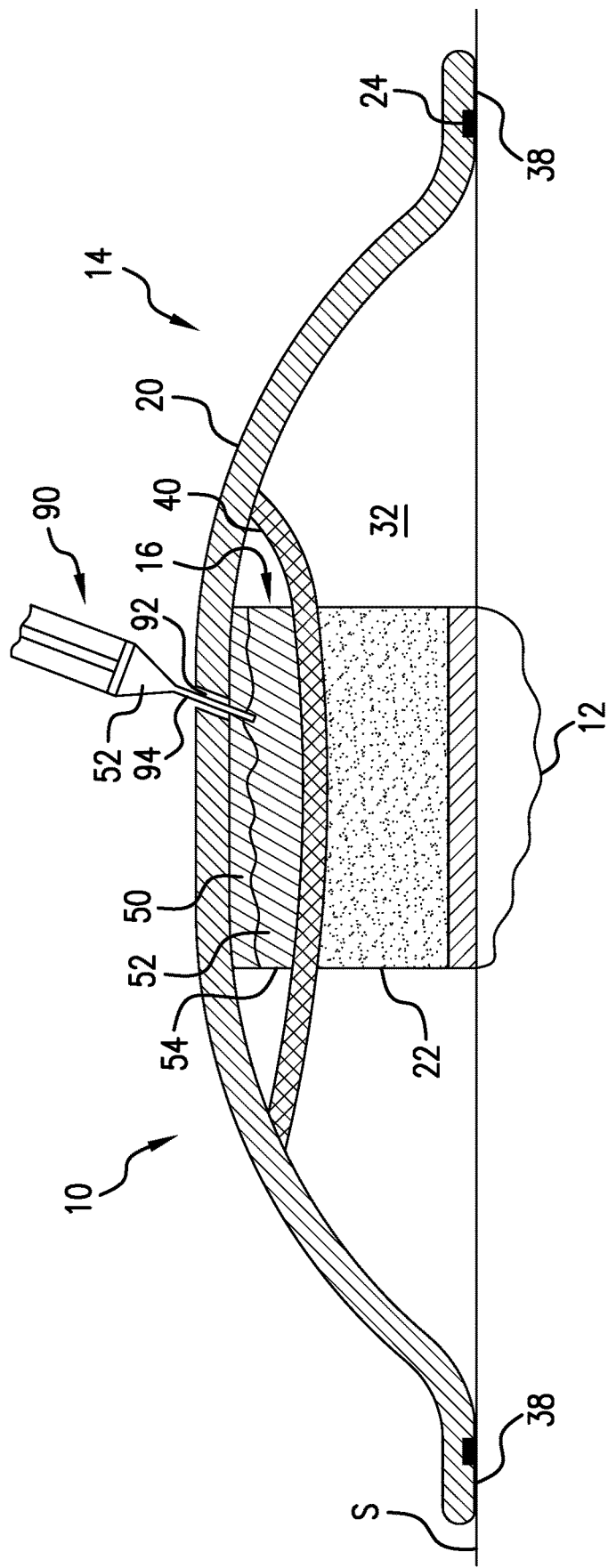
FIG. 5 is a schematic cross-sectional view of another reduced pressure device.

Referring to FIG. 5, the electrolyte solution 52 can be injected into the dressing 14 when reduced pressure therapy is ready to be administered. For example, the electrolyte solution 52 can be injected into the substrate 54 having the reducing agent 50 or into a mass of powdered chemicals making up the reducing agent 50 by a syringe 90. An injection port 92 can be disposed on the drape 20 for guiding a user for injecting a needle 94 of the syringe 90 into the substrate 54 or mass of powdered chemicals making up the reducing agent 50. When reduced pressure is ready to be administered, the user injects the electrolyte solution 52 into the substrate 54 to impregnate the substrate 54 with the electrolyte solution 52 or into the mass of powdered chemicals making up the reducing agent 50. Once the reducing agent 50 is wetted with the electrolyte solution 52, the reactor 16 begins to react with the selected gas in the enclosed volume 32 and consuming the selected gas. After finishing injecting the electrolyte solution 52 into the dressing 14, the injection port 92 can be covered with a thin film in a similar manner to the slit 70 shown in FIG. 4.

Figure 6:
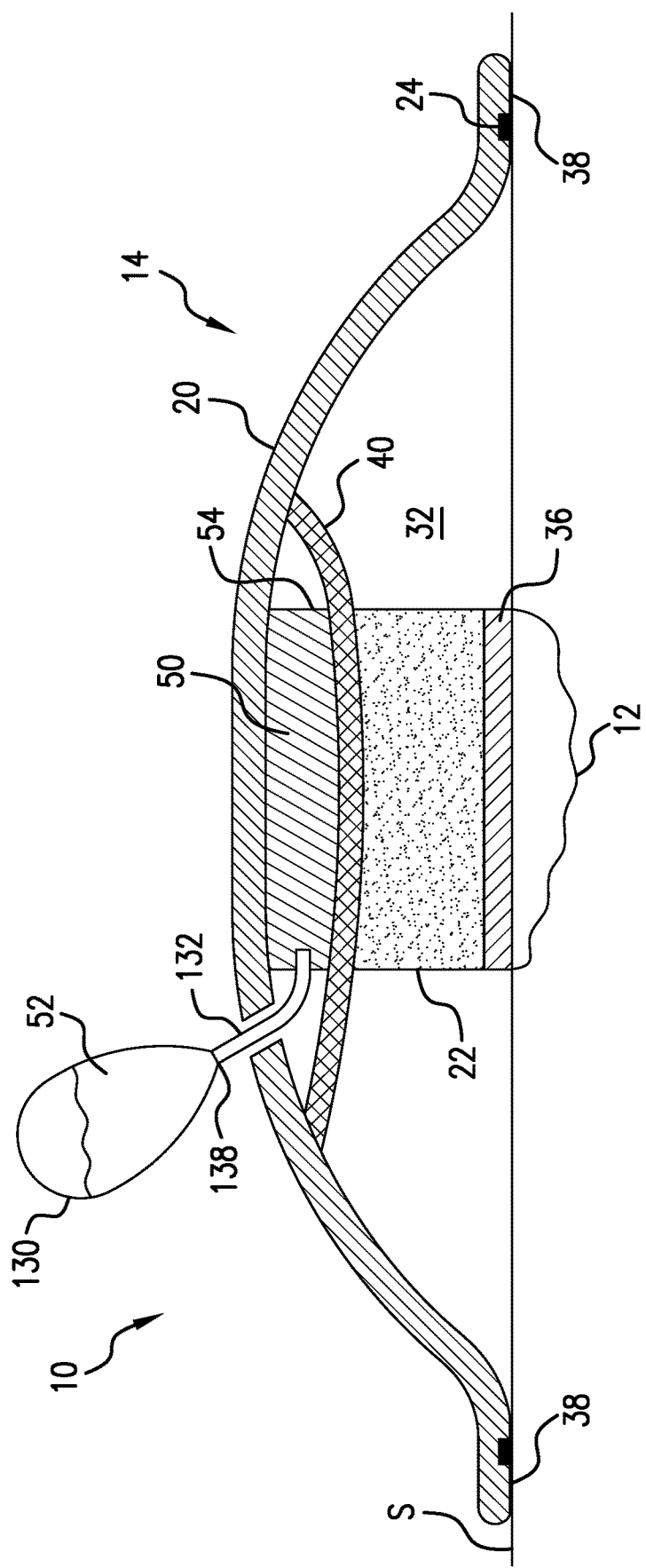
FIG. 6 is a schematic cross-sectional view of another reduced pressure device.

In yet another embodiment, with reference to FIG. 6, the electrolyte solution 52 can be stored in a flexible chamber 130 until the reduced pressure therapy is ready to be administered. The flexible chamber 130 can be located externally from the dressing 14. The flexible chamber 130 is connected to the substrate 54 having the reducing agent 50 or the mass of powdered chemicals making up the reducing agent 50 by a flow conduit 132. The flow conduit 132 can further include a seal 138. The seal 138 can be located at any portion of the flow conduit 132. When reduced pressure therapy is to be administered, the flexible chamber 130 is pressed and/or squeezed and the flow pressure of the electrolyte solution 52 breaks the seal 138, and the electrolyte solution 52 is delivered to the substrate 54 or the mass of powdered chemicals making up the reducing agent 50.

Figure 7:
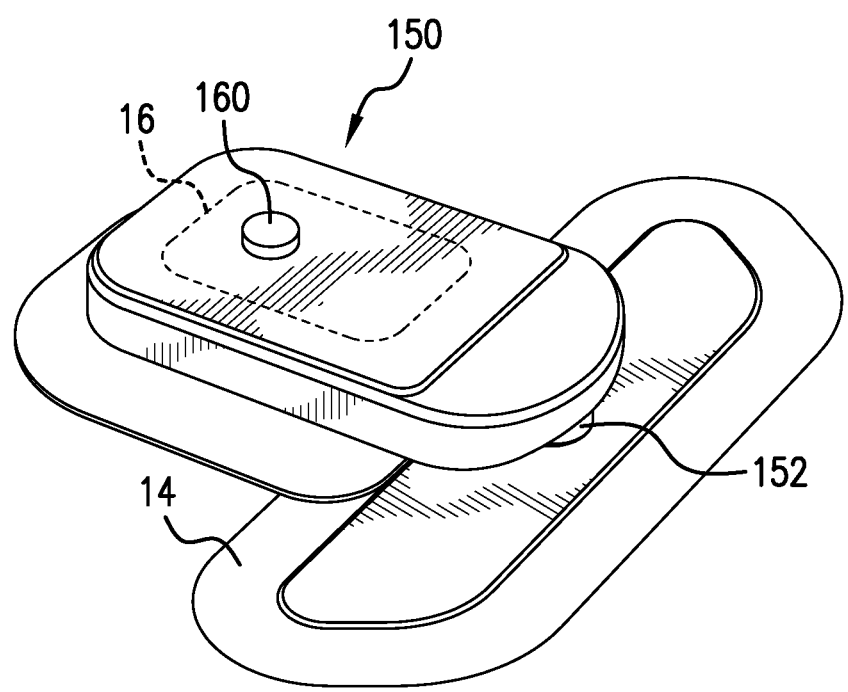
FIG. 7 is a perspective view of a dressing connected with a chemical pump housing.
Figure 8:
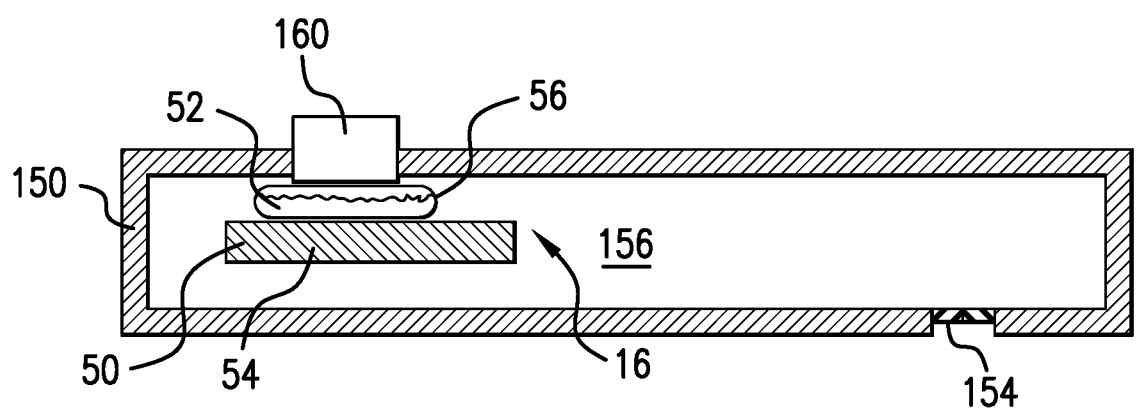
FIG. 8 is a schematic cross-sectional view of the chemical pump housing.

FIG. 7 depicts an example in which the reactor 16 is positioned outside of the dressing 14 while still being positioned with respect to the dressing 14 so as to produce a reduced pressure beneath the dressing 14 when activated. The reactor 16 is positioned within a chemical pump housing 150. The chemical pump housing 150 can either connect directly to a fitting 152 provided on the dressing 14 via a fitting or valve 154 (FIG. 8) on the chemical pump housing 150 or can connect via a hose (not shown) to the dressing 14 via the fitting 152 or something similar. When properly connected with the dressing 14, an inner chamber 156 of the chemical pump housing 150 is in fluid communication with the enclosed volume 32.

Where the chemical pump housing 150 is made from a rigid plastic, a flexible section or button 160 can be disposed on a surface of the chemical pump housing 150. The flexible section or button 160 is preferably disposed on a top surface of the chemical pump housing 150. The flexible section or button 160 can be aligned with the capsule 56 so as to be a pressing location where a user can press to break the capsule 56 containing the electrolyte solution 52. After the capsule 56 is ruptured, the electrolyte solution 52 is delivered to the substrate 54 or mass of powdered chemicals making up the reducing agent 50. Similar to that described above, after the reducing agent 50 is wetted with the electrolyte solution 52, the reactor 16 begins to consume the selected gas in the enclosed volume 32 and the inner chamber 156.

Figure 9:
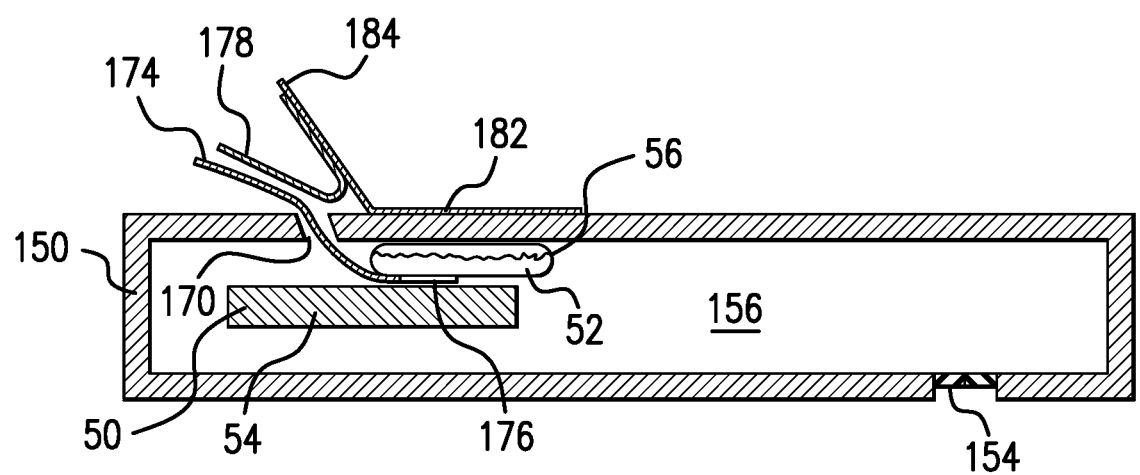
FIG. 9 is a schematic cross-sectional view of an alternative chemical pump housing.

With reference to FIG. 9, a slit 170 is disposed on the chemical pump housing 150 instead of the dressing 14. When the slit 170 is disposed on the chemical pump housing 150, a first pull tab 174 extends from the inner chamber 156 to ambient and is connected to a separable layer 176 of the capsule 56. The separable layer 176 isolates the electrolyte solution 52 within the capsule 56 and from the reducing agent 50. The first pull tab 174, which could also be in the form of a string, can be pulled to remove the first pull tab 174 and the separable layer 176 from the slit 170. When the first pull tab 174 is pulled, the separable layer 176 is removed from the capsule 56 and, if desired, from the inner chamber 156 through the slit 170, exposing the reducing agent 50 to the electrolyte solution 52. After the removal of the separable layer 176, the electrolyte solution 52 is delivered to the reducing agent 50, which begins to react with a selected gas, e.g., oxygen, in the inner chamber 156 and the enclosed volume 32.

Also, a cover layer, which can be a thin film 182, is disposed on the chemical pump housing 150. A second pull tab 178 is connected to the thin film 82, which is placed over and adhered to a portion of the top surface of the chemical pump housing 150. The thin film 182 includes a flap 184 and, as depicted in FIG. 9, the slit 170 is disposed underneath the flap 184. The second pull tab 178 can be connected to or provided as a release layer provided on a bottom surface of the thin film 182 in the region of the flap 184. The release layer covers an adhesive (not visible in FIG. 9) on a bottom surface of the thin film 182. When the second pull tab 178 is pulled, which occurs after the first pull tab 174 has been removed from the slit 170, the second pull tab 178 disconnects the release layer from the flap 184 and the adhesive disposed on the bottom surface of the flap 184 is exposed. The flap 184 is then moved towards the chemical pump housing 150 to cover the slit 170. When the thin film 182 covers the slit 170, the reactor 116 is closed off from ambient and reacts with the selected gas found in the inner chamber 156 and the enclosed volume 32 under the dressing 14. Reduced pressure is therefore developed in the enclosed volume 32.

Figure 10:
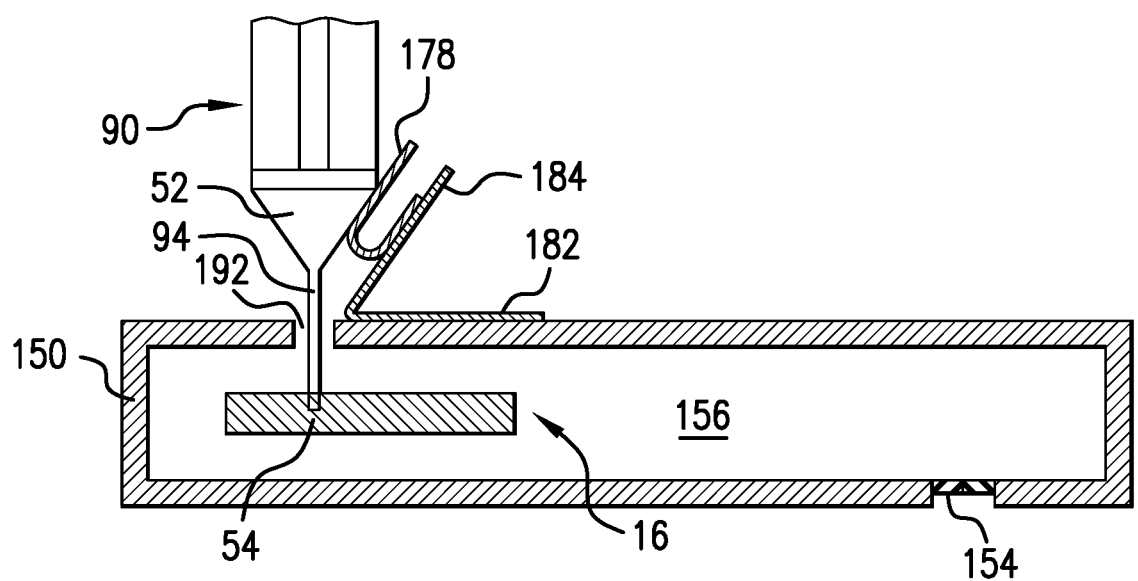
FIG. 10 is a schematic cross-sectional view of an alternative chemical pump housing.

With reference to FIG. 10, the electrolyte solution 52 can be injected into the substrate 54 or mass of powdered chemicals making up the reducing agent 50 through the chemical pump housing 150 when reduced pressure therapy is ready to be administered. An injection port 192 can be disposed on the chemical pump housing 150 for guiding a user for injecting the needle 94 of the syringe 90 into the substrate 54 or mass of powdered chemicals making up the reducing agent 50. When reduced pressure is ready to be administered, the user injects the electrolyte solution 52 into the substrate 54 to impregnate the substrate 54 with the electrolyte solution 52 or into the mass of powdered chemicals making up the reducing agent 50. Once the reducing agent 50 is wetted with the electrolyte solution 52, the reactor 16 begins to consume the selected gas in the enclosed volume 32 and the inner chamber 156 of the chemical pump housing 150. After finishing injecting the electrolyte solution 52 into the dressing 14, the injection port 92 can be covered with the thin film 182 and the flap 184 in a similar manner to the slit 170 shown in FIG. 9. Also, the electrolyte solution 52 stored in the flexible chamber 130 shown in FIG. 6 can deliver the electrolyte solution 52 through the injection port 192 in the chemical pump housing 150 similar to the syringe 90.

Unlike solutions that package a reactor in a hermetically sealed foil packet, the electrolyte solution is shielded from the reducing agent until reduced pressure therapy of the dressing. It will be appreciated that various of the above-disclosed embodiments and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A reduced pressure device comprising:
a dressing configured to cover a dressing site and define an enclosed volume beneath the dressing and around the dressing site; and
a reactor disposed with respect to the dressing so as to produce a reduced pressure beneath the dressing when activated, the reactor including a reducing agent and an electrolyte solution,
wherein the electrolyte solution is configured to be selectively delivered to the reducing agent, and the reactor begins to react with at least one selected gas in the enclosed volume after the electrolyte solution is delivered to the reducing agent to consume the at least one selected gas within the enclosed volume;
wherein the electrolyte solution is stored in a rupturable capsule positioned adjacent to the reducing agent, and the rupturable capsule is configured to rupture to deliver the electrolyte solution to the reducing agent;
wherein the rupturable capsule is configured to rupture by way of pulling a tab operatively connected with the rupturable capsule;
wherein the reactor is disposed beneath the dressing, wherein the dressing includes a slit in which the tab extends from beneath the dressing to an ambient environment, the tab being configured to be pulled through the slit; and
wherein the dressing includes a cover layer having an adhesive disposed thereon, the cover layer being configured to be applied over the slit to cover the slit after removal of the tab.

2. The reduced pressure device of claim 1, wherein the reduced pressure device further includes a chemical pump housing connected to the dressing, the chemical pump housing including an inner chamber in which the reactor is disposed.

3. The reduced pressure device of claim 2, wherein the rupturable capsule is positioned in the inner chamber adjacent to the reducing agent.

4. The reduced pressure device of claim 1, further comprising a substrate having the reducing agent.

5. The reduced pressure device of claim 1, further comprising a second tab disposed to cover the adhesive on the cover layer; wherein removal of the second tab exposes the adhesive for sealing the cover layer over the slit.

* * * * *